(12) United States Patent
Borghese et al.

(10) Patent No.: US 7,929,661 B2
(45) Date of Patent: Apr. 19, 2011

(54) METHOD AND APPARATUS FOR RADIOGRAPHIC IMAGING

(75) Inventors: Nunzio Alberto Borghese, Milan (IT); Iuri Frosio, Sorisole (IT); Eros Nanni, Castel S.Pietro (IT); Gerardo Rinaldi, Milan (IT); Giuseppe Rotondo, Pantigliate-Milan (IT)

(73) Assignee: CEFLA S.C. (IT)

( * ) Notice: Subject to any disclaimer, the term of this patent is extended or adjusted under 35 U.S.C. 154(b) by 126 days.

(21) Appl. No.: 12/479,254

(22) Filed: Jun. 5, 2009

(65) Prior Publication Data
US 2009/0310741 A1 Dec. 17, 2009

(30) Foreign Application Priority Data
Jun. 6, 2008 (EP) ..................................... 08157813

(51) Int. Cl.
- *A61B 6/14* (2006.01)
- *A61B 6/04* (2006.01)
- *G01N 23/04* (2006.01)

(52) U.S. Cl. .............................. 378/38; 378/37; 378/62

(58) Field of Classification Search ................... 378/37, 378/38, 62, 162–166
See application file for complete search history.

(56) References Cited

U.S. PATENT DOCUMENTS

| | | | |
|---|---|---|---|
| 4,831,645 A | 5/1989 | Guenther et al. | |
| 4,856,038 A | 8/1989 | Guenther et al. | |
| 4,907,251 A | 3/1990 | Mork et al. | |
| 5,425,065 A | 6/1995 | Järvenin | |
| 6,081,739 A | 6/2000 | Lemchen | |
| 6,510,196 B2 | 1/2003 | Lanér | |
| 6,614,875 B2 | 9/2003 | Suuronen | |
| 7,103,141 B2 | 9/2006 | Sonobe et al. | |
| 7,133,496 B2 | 11/2006 | Wilson | |
| 2002/0085672 A1 | 7/2002 | Ganin et al. | |
| 2003/0007602 A1 | 1/2003 | Sonobe et al. | |
| 2004/0096035 A1 | 5/2004 | Yamazaki et al. | |
| 2005/0031080 A1 | 2/2005 | Klingenbeck-Regn et al. | |
| 2006/0213996 A1 | 9/2006 | Crucs | |
| 2007/0172102 A1 | 7/2007 | Hempel | |

(Continued)

FOREIGN PATENT DOCUMENTS

DE 3632878 A1 3/1988

(Continued)

OTHER PUBLICATIONS

Whitaker, R.T, A Level-Set Approach to Image Blending, Image Processing, IEEE Transactions on, vol. 9, Issue 11, Nov. 2000 pp. 1849-1861.

(Continued)

*Primary Examiner* — Irakli Kiknadze
(74) *Attorney, Agent, or Firm* — St. Onge Steward Johnston & Reens LLC

(57) ABSTRACT

A radiographic X-ray apparatus is equipped with multiple devices for the acquisition of anatomical data, in particular cameras. These devices are used to facilitate and automate the imaging process, providing: before exposure the automated identification of the specific anatomical features of the patient and the optimized presetting of the exposure technique factors and projection geometry, tailored on the actual anatomy of the patient; during exposure the optimized X-ray dose modulation, either automatically or selected by the operator, in order to correctly expose the various regions of interest, and accordingly impart reduced dose to other body parts, according to the actual anatomy of the patient and imaging requirements; after exposure the possibility to complement the radiographic image with additional information about the internal and external anatomy, providing valuable tools for the medical analysis and diagnosis.

28 Claims, 5 Drawing Sheets

U.S. PATENT DOCUMENTS

2007/0183567 A1    8/2007    Rotondo et al.
2008/0101538 A1    5/2008    Schliermann

FOREIGN PATENT DOCUMENTS

| | | |
|---|---|---|
| DE | 102004042790 A1 | 3/2006 |
| EP | 1216661 A2 | 6/2002 |
| EP | 1624411 A2 | 2/2006 |
| EP | 1772101 A1 | 4/2007 |
| JP | 2001346796 A | 12/2001 |
| WO | 03010555 A2 | 2/2003 |

OTHER PUBLICATIONS

Blanz, V.; Vetter, T., A Morphable Model for the Synthesis of 3D Faces, SIGGRAPH (1999) Conference Proceedings, 8 pages.

Frosio, I.; Borghese, N. A.: A New Real Time Filter for Local Exposure Correction in Panoramic Radiography, Medical Physics, vol. 33, No. 9, Sep. 2006, p. 3478-3488.

Elbakri, I. et al.: Automatic Exposure control for a slot scanning full field digital mammography systems, Med. Phys. 32, p. 2763-2770, 2005.

Frosio, I.; Ferrigno, G.; Borghese, N. A., Enhancing digital cephalic radiography with mixture models and local gamma correction, IEEE Trans Med Imaging. vol. 25 No. 1, Jan. 2006, p. 113-121.

Extended European Search Report; EP 08 15 7813; Dec. 19, 2008; 9 pages.

Blanz, V.; Vetter, T., Face Recognition Based on Fitting a 3D Morphable Model, IEEE Transactions on Pattern Analysis and Machine Intelligence, vol. 25 No. 9, p. 1063-1074, 2003.

Sinha, P. et al. in: Face Recognition by Humans: 19 Results All Computer Vision Researchers Should Know About, Proceedings of the IEEE, vol. 94, No. 11, Nov. 2006, p. 1948-1962.

Zhao, W. et al. Face Recognition: A Literature Survey, ACM Computing Surveys, 2003, p. 399-458.

Goto, T. et al., Facial feature extraction for quick 3D face modeling, Signal Processing: Image Communication, vol. 17, No. 3, Mar. 2002, p. 243-259(17).

Saber, E.; Tekalp, A. M., Frontal-view face detection and facial feature extraction using color, shape and symmetry based cost functions, Pattern Recognition Letters, vol. 19, Issue 8, Jun. 1998, p. 669-680.

Johnson, L.S. et al., Initial clinical experience with a video-based patient positioning system, International Journal of Radiation Oncology, Biology, Physics, vol. 45, Issue: 1, Aug. 1, 1999, p. 205-213.

Tisse, C. et al., Person identification technique using human iris recognition (2002), IEEE Trans. Patt. Anal. Mach. Intell., 2002; 6 pages.

Fox, N.A. et al., Robust Biometric Person Identification Using Automatic Classifier Fusion of Speech, Mouth, and Face Experts, IEEE Trans. On Multimedia, vol. 9, Issue 4, Jun. 2007 p. 701-714.

Fox, N.A.; Reilly, R.B., Robust multi-modal person identification with tolerance of facial expression, 2004; 6 pages.

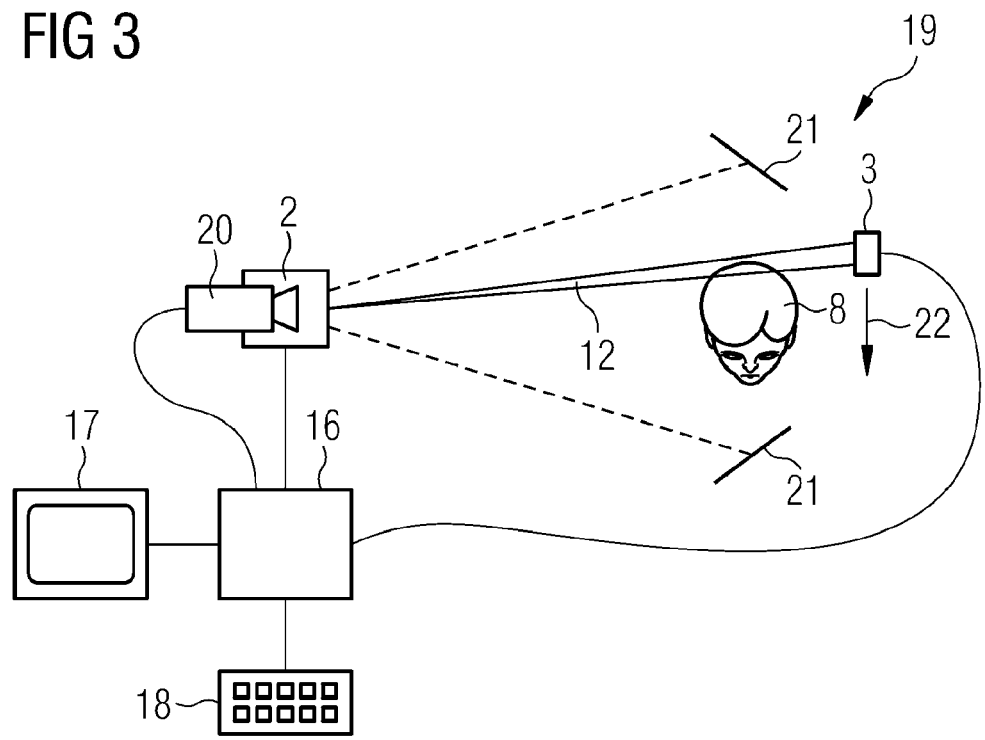
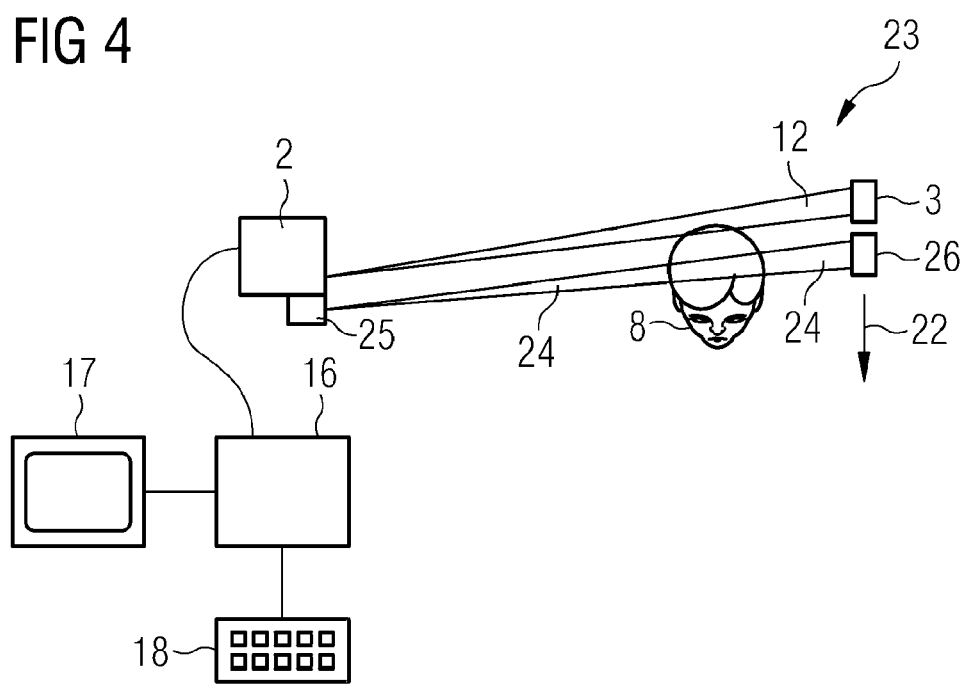

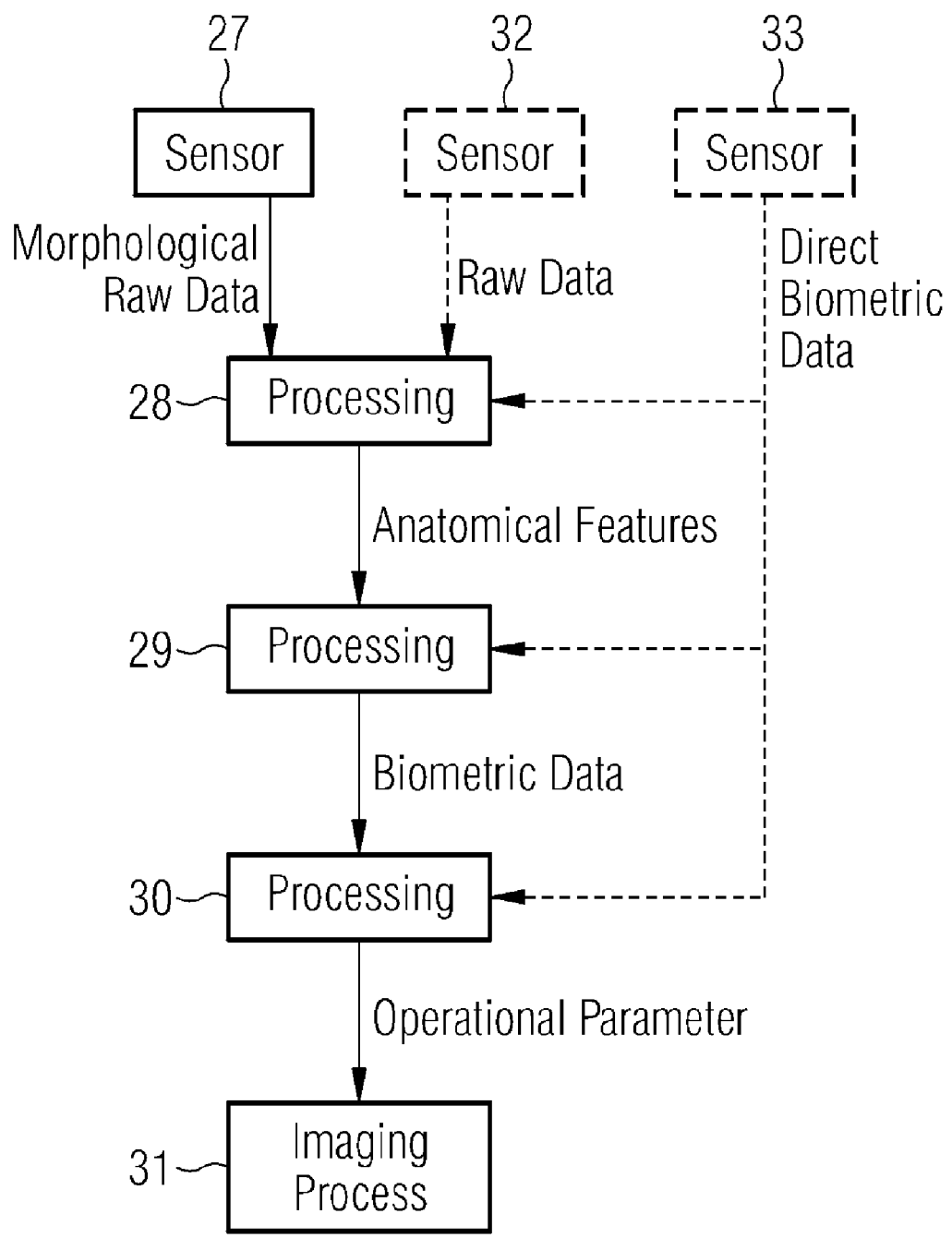

METHOD AND APPARATUS FOR RADIOGRAPHIC IMAGING

CROSS-REFERENCE TO RELATED APPLICATIONS

This application claims priority of European Application No. 08 157 813.0 filed on Jun. 6, 2008. The disclosure of this application is hereby incorporated by reference in its entirety, as part of the present disclosure.

FIELD OF THE INVENTION

The invention relates to a method for radiographic imaging by means of high energy radiation comprising the method steps of:
positioning a patient by means of a positioning system adapted for positioning a patient with respect to an imaging system comprising a high energy radiation source and a high energy radiation detector;
acquiring multiple biometric data about the actual anatomy of the patient using at least one data acquisition device;
using the imaging system for acquiring radiographic images by an imaging process and setting at least one operational parameter of the imaging process in dependency of the multiple biometric data.

BACKGROUND OF THE INVENTION

The invention further relates to an apparatus for implementing the method.

Such a method and such an apparatus are known from U.S. Pat. No. 7,103,141 B2. According to the known method, a head support is used for determining exposure values in an X-ray cephalometric apparatus. The head support comprises support elements that can be positioned against the head of a patient, preferably against the cranial part of the head. The position of the support elements is determined by mechanical sensors. From the position of the support elements, the size and the position of the head of the patient can be derived. In particular, the distance between the ears of the patient and the position of the nasion can be determined. According to the data obtained a modulation of the radiation intensity or scanning speed of the X-ray exposure either automatically or according to a predefined profile is performed during the imaging process.

A similar method is disclosed in U.S. Pat. No. 6,510,196 B2. According to the known method various alternative size measurements of the head of a patient are used to estimate the bone thickness of the head. According to the data obtained for the size and position of the head, appropriate values of the current and voltage applied to the X-ray tube as well as appropriate values of the exposure time are proposed to the operator on a display. The operator may then accept the proposed values or change the actual settings of these operational parameters.

In the known methods, the settings of the operational parameters are chosen based on the aperture of the head support. This approach is highly affected by inaccuracy due to the differences in age, sex and height. Moreover, positioning the patient correctly inside the head support is a time consuming step, and the comfort of the patient is not optimized due to the head support.

U.S. Pat. No. 4,856,038 discloses a method for adjusting a panoramic X-ray apparatus. In the known method, the most appropriate dental arch profile for the actual patient is identified by a subjective evaluation of the operator supported by a tablet on which the actual patient dental arch profile can be drawn by the operator. This will be used by the system to drive the movements during the panoramic imaging and hence to adjust the layer in focus around the selected dental arch profile.

According to other known methods the operational parameters of the X-ray exposure are automatically controlled during the imaging process.

In the methods according to US 2004/0096035 A1, the radiation dose is increased or decreased by a constant factor by an automatically exposure control (=AEC) system, on the basis of the signal measured along the first acquired columns of a panoramic radiography. Other refined AEC systems, including closed-loop operation, have been proposed for digital mammography in ELBAKRI, I. et al.: Automatic Exposure control for a slot scanning full field digital mammography systems, Med. Phys. 32, p. 2763-2770, 2005.

Also panoramic X-ray equipments of the prior art, such as the one disclosed in U.S. Pat. No. 5,425,065, typically adopt a modulation of the X-ray exposure to compensate the higher absorption in the region of the spine. Such modulation can be either predefined or automatically adjusted by an automatic exposure control during the acquisition process. The result is often not optimal due to lack of adjustment on the specific anatomy and positioning of the actual patient, or due to inaccuracies of the automatic exposure control system. This may generally be corrected by post exposure image processing, aimed at uniformity of the image density along the various regions, but it does not compensate the lack of signal-to-noise ratio due to incorrect exposure, which typically exhibits in vertical bands on the diagnostic image.

Some effective software solutions for correcting a posteriori these defects have been proposed in FROSIO, I.; BORGHESE, N. A.: A New Real Time Filter for Local Exposure Correction in Panoramic Radiography, Medical Physics, Vol. 33, No. 9, September 2006, p. 3478-88. Another method is disclosed in FROSIO, I.; FERRIGNO, G.; BORGHESE, N. A., Enhancing digital cephalic radiography with mixture models and local gamma correction, IEEE Trans Med Imaging. Vol. 25 No. 1, January 2006, p. 113-121.

However, these algorithms cannot guarantee that the signal-to-noise ratio is constant over the entire image. Moreover, they locally modify the statistical properties of the image and this can represent a problem for further processing algorithms applied to these images. Best results could be achieved only by optimizing a priori the X-ray modulation.

U.S. Pat. No. 7,133,496 B2 discloses a method for cephalometric radiography in which an almost correct exposure of both the bone and the soft tissue is obtained by means of some hardware filter applied to the radiographic apparatus, aimed at the reduction of the dose in the soft tissue area.

Such procedures are usually complemented by specific image post processing, aiming to apply a differentiated contrast enhancement gamma for the regions of soft tissues and the regions of bone tissue, as described in EP 1 624 411 A2.

Besides these methods for adjusting the operational parameters of an X-ray apparatus, methods have recently been developed for automatic face recognition systems. An overview can be found in SINHA, P. et al. in: Face Recognition by Humans: 19 Results All Computer Vision Researchers Should Know About, Proceedings of the IEEE, Vol. 94, No. 11, November 2006, p. 1948-1962 and in ZHAO, W. et al. Face Recognition: A Literature Survey, ACM Computing Surveys, 2003, p. 399-458

The publications TISSE, C. et al., Person identification technique using human iris recognition (2002), IEEE Trans. Patt. Anal. Mach. Intell., 2002 and FOX, N. A. et al., Robust Biometric Person Identification Using Automatic Classifier Fusion of Speech, Mouth, and Face Experts, IEEE Trans. On Multimedia, Vol. 9, Issue 4, June 2007 p. 701-714. as well as FOX, N. A.; REILLY, R. B., Robust multi-modal person identification with tolerance of facial expression, 2004 contain further details on face identification.

SABER, E.; TEKALP, A. M., Frontal-view face detection and facial feature extraction using color, shape and symmetry based cost functions, Pattern Recognition Letters, Volume 19, Issue 8, June 1998, p. 669-680 describes a method for detecting human faces based on color and shape information and for locating the eyes, nose and mouth by symmetry based cost functions.

GOTO, T. et al., Facial feature extraction for quick 3D face modeling," Signal Processing: Image Communication, Volume 17, Number 3, March 2002, p. 243-259(17) discloses a method for the three-dimensional face modeling.

A similar method can be found in BLANZ, V.; VETTER, T., Face Recognition Based on Fitting a 3D Morphable Model, IEEE Transactions on Pattern Analysis and Machine Intelligence, vol. 25 no. 9, p. 1063-1074, 2003 and also in BLANZ, V.; VETTER, T., A Morphable Model for the Synthesis of 3D Faces, SIGGRAPH 99 Conference Proceedings.

Vision systems were already proposed in radiotherapy to control the correct alignment of the patient with respect to the X-ray machine. According to JOHNSON, L. S. et al., Initial clinical experience with a video-based patient positioning system, International Journal of Radiation Oncology, Biology, Physics, Volume: 45, Issue: 1, Aug. 1, 1999, p. 205-213 a vision system is used for positioning a patient with respect to reference positions; the position of the patient can then be checked in each moment through a simple image subtraction technique.

A first dental X-ray system equipped with video cameras was disclosed in DE 36 32 878 A1, where the use of video cameras is proposed for the purpose of generating silhouettes of the head of a patient and adjusting the silhouette of an actual position with the silhouette of a desired position of the patient head.

Another dental X-ray system equipped with video cameras is disclosed in JP 2001 34 67 96 A, where the use of a video camera is proposed for verifying or controlling, either manually or automatically, the positioning of a head of a patient.

According to U.S. Pat. No. 6,614,875 B1 a cephalographic X-ray system is equipped with a video camera. In this document, the use of a video camera with the same geometry as the X-ray field is proposed for obtaining cephalographic pictures and side views of the head that can be superimposed by means of reference elements in the head positioning means.

A further dental X-ray system equipped with video cameras is disclosed in US 2007/0183567 A1, where the use of one or more video cameras is suggested for identifying a misalignment of the head with respect to the system by automatic processing and analyzing the video images, and applying a correction of the relevant mechanical parameters guided by reference markers or lines superimposed on the views of the patient.

Finally, WHITAKER, R. T, A Level-Set Approach to Image Blending, Image Processing, IEEE Transactions on, Volume 9, Issue 11, November 2000 pp 1849-1861 discloses a method for blending images.

SUMMARY OF THE INVENTION

Proceeding from this related art, the present invention seeks to provide an improved method and apparatus for the automatic acquisition of radiographic images.

This object is achieved by a method and an apparatus having the features of the independent claims. Advantageous embodiments and refinements are specified in claims dependent thereon.

In the method and in the apparatus, multiple raw data are acquired using the at least one data acquisition device. These raw data are processed to identify specific anatomical features of the actual anatomy of the patient. These specific anatomical features may be the eyes, nose, lips or similar morphological features whose position is not known from the beginning. Thus, a search for the relevant anatomical features is performed. Based on the identified specific anatomical features multiple biometric data can be generated. In the context of this application the multiple biometric data are to be understood as a data set of quantities related to identified anatomical features. In particular, the biometric data may include a single number associated with a unit, for example a width of a head measured in centimeters; the biometric data may also include a multidimensional quantity or a plurality of such multidimensional quantities, for example the position of some anatomical features with respect to a given coordinate system, such as the positions of the center of the eyes or a position of the tip of the nose, or for example a profile such as the profile of a true dental arch; the biometric data may also be a relation of two quantities, for example the ratio of the temple width to the height of the face; the multiple biometric data may further include also other spatial quantities of the identified anatomical features, such as quantified areas or volumes; finally the multiple biometric data may also contain a measurement of a congruence between an anatomical feature and some predefined pattern, for example the deviation of an identified profile, for instance the actual contour of a head, from a predefined standard contour of the head or similar data. The biometric data can then be used to set the operational parameter without any interaction of the operator since the relevant anatomical features are recognized automatically and since the biometric data needed for the control of the imaging process are also automatically retrieved. Since no time consuming manual interaction of an operator is needed for choosing the place where the biometric data have to be taken a plurality of biometric data can be acquired so that the operational parameter can be better adjusted to the actual anatomy of the patient.

In a preferred embodiment a plurality of morphological parameters of the anatomy of the patient are obtained as biometrical data. The morphological parameters are biometric data which refer to features of the outer appearance of the patient such as a contour of the patient or the position or shape of an anatomical feature within a contour such as the position of the eyes, the mouth or the nose or the ears. The morphological parameters can advantageously be used for controlling the imaging process since the position of soft tissue can be accurately determined.

The multiple raw data may also be used to retrieve a profile of the anatomy of the body of the patient. In this context, a profile shall be understood to be a continuous curve or a plurality of subsequent sites. The profile can then be used to vary the operational parameters continuously or at least gradually during the acquisition process in an appropriate way adapted to the specific profile of the anatomy of the patient. Such profiles can be the profile of the true dental arch or the profile of the transition between a hard tissue region and a soft tissue region. The profile can then be used to vary the operational parameters continuously or at least gradually by a plurality of small steps during the acquisition process in an appropriate way adapted to the specific anatomy of the patient. Therefore, the method and the apparatus allow for a fine tuning of the operational parameters in an automatic image acquisition process.

Preferably, morphological raw data are acquired as multiple raw data in a contactless way. In the context of this application the morphological raw data are to be understood as unprocessed raw data relating to the outer appearance of the patient. Devices that acquire morphological data in a contactless way are generally disposed at a distance from the body of the patient. Being disposed at a distance, these devices are able to measure extended features of the anatomy of the patient so that morphological parameters such as the position of the eyes, the mouth or the nose or the ears can be advantageously determined automatically from an extended view of the anatomy of the patient. A further advantage of the contactless acquisition of the anatomical raw data is that any discomfort of the patient is avoided.

In a preferred embodiment, the morphological raw data are acquired by an optical camera adapted for taking views of the actual patient anatomy. Artificial vision systems and associated pattern analysis techniques can advantageously replace the human vision due to the development of advanced algorithms, the increase in computational power in embedded computers and the technological improvement of the compact video cameras which provide good image quality and stability standard high rate interfaces, such as USB2 or IEEE 1394-Firewire, high accuracy, repeatability and speed up of operation procedures versus the corresponding human operations. These cameras are available at reasonable costs and allow the determination of profiles of the imaged parts of the patient's body. Besides optical cameras, also other devices such as devices adapted for taking three-dimensional images, in particular devices which measure the traveling time of an acoustic or electromagnetical signal in the radiofrequency or optical frequency range, or devices arranged for detecting a silhouette of the patient can be used for the contactless acquisition of the morphological data.

The morphological raw data can also be generated by means of a mirror arrangement providing an additional perspective of the patient and can also be complemented by additional biometric data measured by a data acquisition device that is supplying directly additional biometric data, such as a patient weight, a height of a biting point, a temple width, a carpus width and similar anatomical parameter. The morphological raw data retrieved by the contactless data acquisition devices can be calibrated on the basis of these additional points, features or patterns, which can be related or not to the machine geometry. Additional points, features or patterns can be provided for a routine check of the calibration of the data acquisition devices.

Preferably, statistical pattern matching is used for processing the anatomical raw data for identifying the specific anatomical features. By using statistical methods, the probability of reproducing the actual anatomy of the patient can be maximized.

Typically, the raw data and/or biometric data are used to automatically set at least one of the operational parameters according to the anatomy of the patient actually imaged by the apparatus. The parameter may be at least one of the parameters contained in the group of operational parameters including current and voltage of the radiation source, exposure timing and projection geometry, scanning speed of the imaging system and detector sensitivity. Thus, the conditions of the radiation exposure can continuously be adapted to the actual region crossed by the radiation beam.

For minimizing the dose for the patient, the setting of the at least one operational parameter is performed using optimization criteria. One possible criterion is the minimization of the dose applied to the patient under the condition that a given signal-to-noise ratio is obtained for the detector signal.

For adapting the at least one operational parameter continuously to the actual alignment of the radiation beam at least one of the automatically set operational parameters are used as a preset reference for an automatic exposure control method, wherein at the beginning of the exposure time an adjustment of the at least one operational parameter is made by a closed loop control of the operational parameter in dependency of the average detector signal while allowing a limited range of variation around a preset reference value of the operational parameter. By limiting the range of allowable variations, the operational parameter cannot assume values that endanger the health of the patient.

The raw data and/or biometric data can also be used for providing an automatic identification of the patient. If the identity of the patient is known further data on the patient can be retrieved from a database where data on the patient are stored. Such data may include data acquired previously such as previous profiles or previous morphological features relating to the anatomy of the patient. The identity of the patient can also be used for reporting purposes. The radiographic images can further be concatenated with metadata such as the name or other personal data of the patient.

Furthermore, the raw data and/or biometric data can also be used for providing an automatic determination of the patient's true dental arch. In particular, in dental tomography or radiography the layer in focus must be accommodated to the specific morphology of the patient for optimal results. The true dental arch can be used to control the movement of the radiation system for adjusting the layer in focus around the selected dental arch profile. Thus the quality of the radiographic images can be considerably improved over the prior art.

Another important issue in dental radiography is the spine position of the patient. If raw data and/or biometric data are used for an automatic identification of the spine position of the patient and if the identified spine position is used to homogenize the level of exposure of the detector by automatically modulating the radiation intensity profile during the imaging process, the quality of the radiographic images can be improved since the intensity of the radiation can be adapted to the absorption of radiation in the spine region.

In particular in cephalography the transition from soft to bony regions should be known for homogenizing the level of exposure. Therefore, the raw data and/or biometric data are used for providing an automatic identification of the transition from soft to bony tissue in the face of the patient for use in lateral radiographic images of the head of the patient. Furthermore, the identified transition from soft to bony tissue is used to homogenize the level of exposure by automatically modulating the radiation intensity profile during the acquisition of the radiographic images of the skull.

The raw data and/or biometric data can finally also be used for providing the actual protrusion of incisors. If the protrusion of the incisors is known the positioning errors caused by the inclination of the incisors and the deviation between the labial end of the incisors determining the position of the incisors in the positioning system and the root of the incisors which determines the position of the dental arch profile can be automatically corrected. Thus, the errors caused by the inclination of the incisors can be avoided.

In a preferred embodiment, the raw data and/or biometric data can be used to provide a two-dimensional or three-dimensional display of the patient's anatomy thus enabling the operator to limit the imaging process to a region of interest selected by the operator on the display of the patient's anatomy. The selected region of interest can then be used to control the imaging process automatically, in order to perform either a partial acquisition limited to the region of interest or an acquisition with a differentiated operational parameter inside or outside of the region of interest, according to the preference of the operator.

The raw data and/or biometric data can also be used for processing the radiographic images after the acquisition process of the radiographic images has been terminated. For example, the information on the profile can be used for adjusting the contrast of the radiographic images after the acquisition process has been finished or superimposing parts of the optical image on the radiographic image.

The output of the processing of the raw data and/or biometric data can finally also be used for providing additional information supporting the medical diagnosis.

In another particular embodiment, the biometric data include the body height of the patient and at least one additional biometric parameter. Thus a basic adjustment of the operational parameters can be performed replacing the usually manual adjustment of the operational parameters to the body height of the patient. Since the size of the body parts to be examined by radiation is critical, the body height of the patient is an important measure for adjusting the operational parameters of the radiation system.

The body height of the patient can be preferably retrieved by the height at which the positioning system must be adjusted for a particular patient. Thus, the size of the patient can be simply and reliably determined.

The method and the apparatus are preferably used for dental panoramic radiography, dental tomography, cephalography or mammography.

BRIEF DESCRIPTION OF THE DRAWINGS

Further advantages and properties of the present invention are disclosed in the following description, in which exemplary embodiments of the present invention are explained in detail based on the drawings:

FIG. 3 shows a schematic view from above on another modified embodiment;

FIG. 4 shows a schematic view from above on a further modified embodiment;

FIG. 5 shows a flow diagram of the method of operation of the embodiments in the preceding figures;

DETAILED DESCRIPTION OF THE INVENTION

Figure 1:
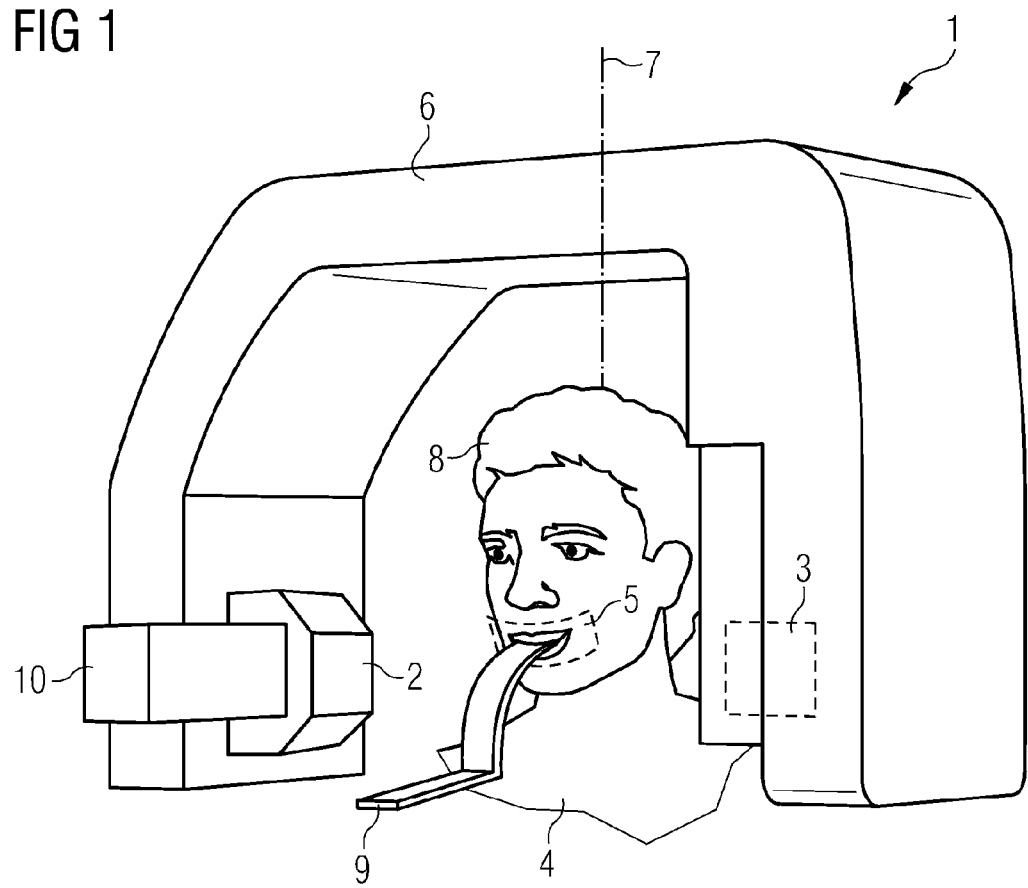
FIG. 1 shows a perspective view of one embodiment of the present invention, wherein a face of a patient is surveyed by a frontal video camera while the patient bites a bite unit.

FIG. 1 shows a apparatus 1 for panoramic dental radiography that comprises a X-ray tube 2 and an X-ray detector 3 for detecting the radiation crossing the body of the patient 4. The detector 3 may be a digital X-ray detector 3 that comprises a matrix of sensible elements or so called pixels, often covered by X-ray detecting scintillator material. Linear shaped area detectors provide the most economic solution to realize a digital radiographic apparatus. For instance, they are widely used to build orthopantomographs aimed to dental radiography. In this case, both the detector 3 and the tube 2 perform a trajectory in the three-dimensional space focusing on a specific target surface 5, for instance the dental arch of the patient 4. For performing the trajectory, the tube 2 and the detector 3 are attached to a support structure 6 that can be rotated around a vertical rotation axis 7 aligned onto a head 8 of the patient 4. For keeping the head 8 of the patient 4, in particular the dental arch of the patient 4 as stationary as possible, a fixing unit 9 is provided with the apparatus 1. The fixing unit comprises a bite block that the patient 4 can introduce into the mouth. While the patient 4 bites on the bite block the dental arch of the patient 4 is kept stationary during the image acquisition process.

Image quality is fundamental to achieve the best clinical results in digital radiography. To achieve a satisfying image quality, several acquisition parameters, for instance the X-ray exposure profile or the position of important anatomical structures, have to be set taking in consideration the actual anatomy of the patient 4. In clinical practice, these parameters are set by the operator either manually or following some golden rule, which may not lead to optimized results for the specific patient 4.

In dental radiography, the operator has to accomplish various critical tasks, which may highly affect the diagnostic value of any acquired radiography. Among others, these tasks are the positioning of the patient 4, the identification of the size of the patient 4, the identification of reference anatomical points, the selection of the anatomical region of interest, the control of the stability of the patient during X-ray exposure, as well as the recognition of the patient's identity.

Based on the subjective evaluation of the size of the patient 4, for instance, the operator may set operational parameters of the radiographic apparatus, which may lead to an inadequate diagnostic image. Estimating the size of the patient 4 also constitutes a time consuming procedure.

Other acquisition parameters are often fixed by the producer of the radiographic apparatus, for instance, the modulation of the X-ray intensity profile during the acquisition of a panoramic radiography.

The modulation of exposure is a general problem in radiography, as the dose should be adapted to the local tissue crossed by the beam, so that the detector receives enough signal, avoiding at the same time the delivery of an excessive dose to specific anatomical structures.

For instance, in panoramic radiography the X-ray dose is generally increased in correspondence to the spine, to obtain a uniform exposure; the modulation is performed according to a predefined exposure pattern, which is not necessarily optimal for any patient 4. Moreover, because of small displacements of the patient 4, the spine position may be shifted with respect to its reference position resulting in images of low quality, if the displacement is not compensated. A typical artifact is represented by a series of stripes appearing in the image.

The apparatus 1 for dental radiography is equipped with a biometric system, which automates various procedures which have to be carried out before radiographic acquisition, with the aim of optimizing the image quality. The biometric system may include an artificial vision system and may additionally comprise several sensors or three-dimensional scanners, which provide a multiplicity of biometrical data including lengths, areas, volumes, weights and morphological data such as two-dimensional views and three-dimensional models which can be processed for obtaining biometric data, in particular specific morphological parameters.

In FIG. 1 only a single video camera 10 is shown. The artificial vision system, however, can also be based on a set of one or more two-dimensional cameras, fixed or moving around the patient 4. In the latter case the cameras could be mounted on the common support structure 6 for the X-ray tube 2 and the detector 3. Such an apparatus can provide a set of two-dimensional images or reconstruct the three-dimensional surface of the head 8 of the patient 4.

In addition, the apparatus can be particularly arranged for determining the body height of the patient 4 by measuring the height of the fixing unit 9 since the height of the fixing unit 9 above floor depends on the body height of the patient 4.

Figure 2:
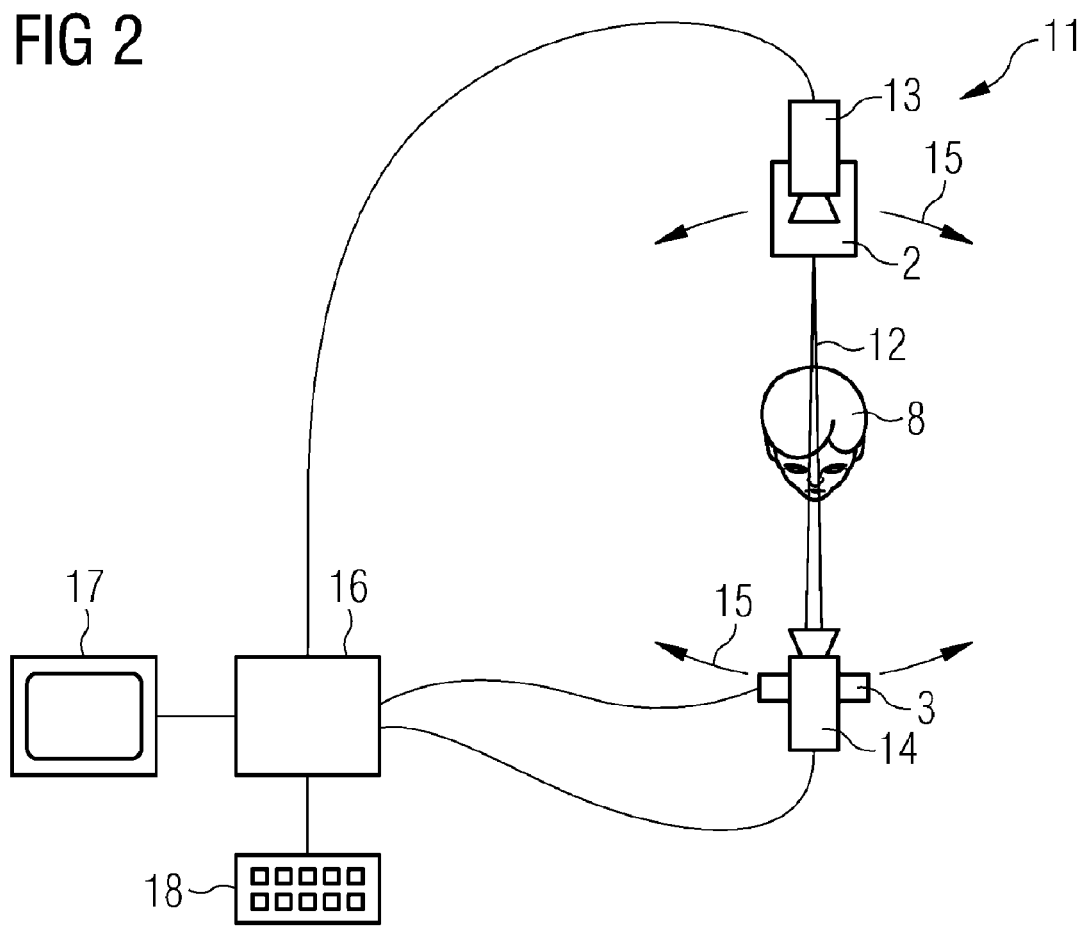
FIG. 2 shows a schematic view from above on a modified embodiment.

In FIG. 2 another example is depicted. FIG. 2 shows a schematic view from above on an apparatus 11 for narrow-beam tomography by a narrow X-ray radiation beam 12. The tube 2 and the detector 3 of apparatus 11 are equipped with cameras 13 and 14 mounted onto the tube 2 and the detector 3. Both cameras 13 and 14 can be used to locate the position of the spine of the patient 4 and the position and the profile of the dental arch. Thus the specific anatomy of the patient 4 can be taken into account while moving the tube 2 and the detector 3 on a trajectory 15 for taking tomographic images of the dentition of the patient 4. For the analysis of the images taken by the cameras 13 and 14, the cameras 13 and 14 are connected to a processing unit 16 which is also provided with a display unit 17 and input devices 18, such as a keyboard. For controlling the imaging process the processing unit 16 is also connected with the tube 2, the detector 3 and a drive system for moving the tube 2 and the detector 3 on the trajectory 15.

FIG. 3 shows another apparatus 19 for cephalometric imaging. In the apparatus 19 the beam 12 has the shape of a fan located in a vertical plan. The apparatus 19 is further provided with a stationary video camera 20 that is disposed next to the tube 2. Furthermore, additional mirrors 21 are provided, so that the camera 20 is able to record views of the head 8 from three sides, namely a front side view, a back side view and a lateral view. From the views the anatomy of the head 8 of the patient 4 can be derived and the operational parameters of the imaging process gradually adjusted to the anatomy of the cranial region actually crossed by the beam 12 while the detector 3 and the beam 12 are moving in a direction 22. As achieving a correct exposure of both bony and soft tissues is critical in cephalography, a good visualization of both soft and hard tissues is particularly advantageous.

It should be noted that the cameras 10, 13, 14 or 20 can be video cameras or photo cameras.

FIG. 4 depicts an apparatus 23, which is also used for cephalometric imaging. In the apparatus 23, the X-ray beam 12 generally has the shape of a fan located in a vertical plan. Associated with the beam 12 is a light beam 24, which might also have the shape of a fan located in a vertical plane. The vertical plane of the light beam 24, which is inclined with respect to the plane of the X-ray beam 12 and advances the X-ray beam 12 with respect to the moving direction 22. The light beam 24 is generated by a light source 25 located next to the tube 2 and detected by a photodetector 26, which preferably comprises an linear array of detector elements. During the imaging process the X-ray beam 12, the light beam 24, the X-ray detector 3 and the photodetector 26 move together in the direction 22. At the beginning of the imaging process the photodetector 26 is fully illuminated, but is only partially illuminated when the photodetector becomes obscured by the head 8 of the patient 4. The silhouette such acquired can be used for adjusting the exposure of the soft tissue of the patient 4.

In the following the various apparatus 1, 11, 19 and 23 are shortly referred to as the apparatus. Furthermore, by referring to the set of cameras we refer to any one of the cameras 10, 13, 14 and 20 or the photo detector 26.

In the following, the use of the data acquired by the set of cameras will be explained in more detail referring to FIG. 5. According to FIG. 5 a sensor 27 is used for retrieving morphological raw data relating to the anatomy of the patient 4. If any camera of the set of cameras is used as sensor 27, the morphological raw data will be images of the patient 4 taken by the camera. By a subsequent data processing 28 anatomical features are identified based on the morphological raw data. These anatomical features can be the contour of a face of the patient 4 or other anatomical landmarks such as the eye, the ears, the nose or the mouth of the patient 4. Therefore, a search for the anatomical features is performed during the data processing 28. Once the anatomical features are identified, biometric data are derived from the morphological raw data by further processing 29. The further processing 29 results in biometric data such as spatial coordinates of the anatomical features. For example, the processing 29 may result in the position of a central point of the eyes or the position of the nasion with respect to the coordinate system or may also result in absolute biometric data such as the width of the head 8 measured between the ears of the patient. Finally, operational parameters are obtained by processing 30 the biometric data. The operational parameter is finally used for an imaging process 31. During the imaging process the radiographic images of the patient are taken.

The sensor 27 is acquiring the morphological raw data in a contactless way. It should be noted, however, that the raw data may also include data which are acquired in contact with the patient. Accordingly an additional sensor 32 may be provided with the apparatus 1, 11, 19 and 23 for the acquisition of additional raw data in contact with the patient 4. These additional raw data may particularly be data which relate to the movement of the patient 4 during the acquisition of the morphological raw data by the sensor 27. Thus, the sensor 32 can be a speed sensor or an accelerometer Furthermore it should be noted that biometric data directly supplied by a sensor 33 can be used for the processing 28 and the processing 30. These data can be a length, height or weight measured by suitable sensing devices in contact with the patient 4. These direct biometric data can be used among other purposes for calibration purposes or for consistency checks.

In the embodiments depicted in the FIGS. 1 to 4 any camera of the set of cameras can be used to automatically estimate the size of the patient 4 and consequently the operational parameters which optimize the acquisition process of the radiographic apparatus. The set of cameras may further be used to automatically recognize the identity of a patient 4, to provide color images, which can be used by the operator to select a particular region of interest and to estimate the shape and the size of the dental arch of the patient 4.

It is assumed that an accurate calibration procedure is carried out so that the acquired morphological raw data, for instance the two-dimensional or three-dimensional views acquired by the set of cameras, are referred to a known reference system stationary with the apparatus.

The data acquisition of the morphological raw data can be replaced or integrated with other biometrical data from local anatomical measurements, like for instance, the measurement of the wrist width, patient height and weight and temple width.

Pattern recognition techniques process these anatomical data to compute the position of several anatomical features of the head 8, which are used to optimize the process of the radiographic acquisition.

The most refined pattern analysis approaches are based on statistical analysis and a combination of the previously introduced techniques: for instance, they permit to reliably recognize a face among a dataset of face images through the analysis of the facial features. For recognizing faces, basic pattern analysis approaches are used to individuate a single feature of the face, for instance an eye or a mouth. When a set of features is considered, the basic approaches can be used to individuate the features; the correct constellation of the features is then selected between the candidate constellations, using some statistical criteria. For instance, there is a null probability for the mouth to lie over the eyes. Thus, a statistical approach based on constellation, is more reliable than a simple set of basic approaches for single feature identification.

Depending on the sensors used and on the intended use of the system, various methods can be used to operate the apparatus.

According to a first method, the apparatus uses biometric data, for instance the structure of anatomical surfaces or fingerprints, to identify the identity of the patient 4.

The identification of the patient 4 can be based on biometric data derived from different sensors. Independently from the kind of sensors used, the data of the patient 4 have to be kept stored in a database. Therefore, a procedure is preferably implemented to record these data, when the patient 4 approaches the apparatus for the first time. Security procedures are adopted to ensure adequate storage and retrieval of patient data to avoid mix up and confusion. Typical patient data include personal data as well as radiographic images and intra oral and extra oral pictures taken with a general purpose or dental camera.

In a preferred embodiment of the first method, the apparatus is equipped with a set of cameras, which capture the face of the patient 4. Any known algorithms can be used to individualize the identity of the patient 4 from the optical images.

In another modified embodiment of the first method, the apparatus is also equipped with a three-dimensional scanner. In this case, three-dimensional data can be used to increase the reliability of the patient recognition system, as specific morphological measurements are available.

In other embodiments, the apparatus may be equipped with a fingerprint sensor or a voice sensor or an iris recognition sensor. Each of these sensor provide sufficient data to identify the patient 4. Other biometric surveying systems can be used as well.

Thus, a particular advantage of the first method is that it provides the opportunity of an automated verification of the patient identity.

A second method relates to the automatic identification of the size of the patient 4 and the computation of the corresponding operational parameters for the acquisition of an X-ray image.

In the second method, the apparatus uses multiple anatomical data of the patient 4 to identify the size of the patient 4 and preferred associated operational parameters for the X-ray imaging process. The method uses several anatomical parameters, as for instance a facial contour, a facial area, as well as the height or weight of the patient 4 to compute and provide as output a classification of the size and/or bone thickness of the head 8 of the patient 4. These values might be used by the clinician or also automatically used by the system to set up the operational parameters of the imaging process.

A particular advantage of the second method is that it provides a quantitative evaluation of the size of the patient 4 and the associated operational parameters independent of the skills and the actual state of fatigue of the operator.

In a preferred embodiment of the second method, a panoramic radiography is acquired. In this case, the patient 4 has to be accurately positioned inside the apparatus by the clinical operator. The used apparatus might be similar to the apparatus 1 depicted in FIG. 1. The positioning of the patient 4 may require that the patient 4 bites on a bite block of the fixing unit 9 or presses his head against any other head resting constraint. Once the patient 4 has been positioned, the face of the patient 4 is surveyed by the camera 10 positioned in front of the face of the patient 4, as shown in FIG. 1. Since the patient 4 is positioned in a standard position, its distance d from the optical focus of the camera 10 is constant, independently from the actual patient 4; as a consequence, also the magnification factor of the camera 10 surveying the face of the patient 4 does not depend on the patient 4.

The frontal image of the patient 4 can be processed by a processing unit similar to the processing unit depicted in FIGS. 2 and 3 to estimate the anatomical parameters of the face of the patient 4, in particular the size of the face of the patient 4.

Figure 6:
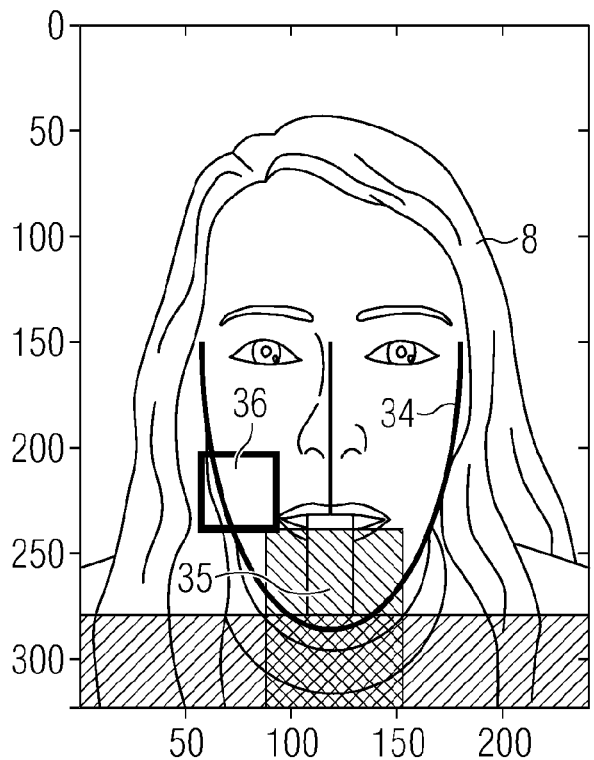
FIG. 6 illustrates the fitting of the patient's frontal profile through a parametric curve, in particular an hyperellipse together with the identification of a region of interest.
Figure 7:
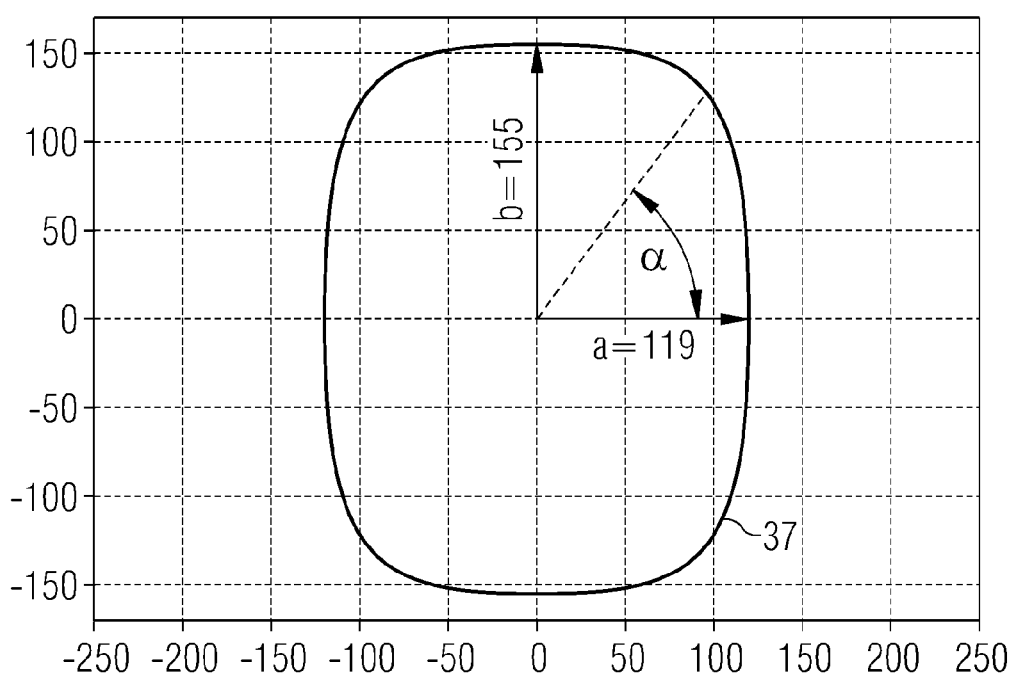
FIG. 7 demonstrates a typical hyperellipse used to fit the shape of the patient's face on a frontal view.

Background subtraction is one of the possibilities which can be employed to determine the contours of the face: an image without any patient 4 is taken first. This image constitutes the background image. Once the patient 4 has been positioned in place, another image is taken and subtracted to the background image. The difference image contains the outline of the patient 4, which provides an estimate of its size. However, due to shadows, this image is often irregular. Moreover, certain types of hair styles, do not allow estimating the true shape of the forehead and of the head 8. One possibility is therefore to consider only the lower part of the face and to regularize the difference image as in GOTO et al. This can, for instance, be achieved by fitting a suitable fitting curve 34, like an ellipse, a spline or a superellipse, to a contour of the difference image as depicted in FIG. 6. The shape of the face can also be represented, for instance, by a hyperellipse 37 as depicted in FIG. 7.

An alternative approach uses no difference image, as in such an image a chin region 35 may not be visible. Instead, the alternative approach operates directly on the acquired raw image. The gradient of the raw image is computed to enhance the face outline as in GOTO et al. and the shape of the face is then fitted through an adequate curve model. From the parameters of the fitted curve and the magnification factor, the size of the face of the patient 4 is then estimated. These procedures are suitable to real-time processing on a processing unit formed by an embedded computer.

Another approach for estimating the anatomical parameters and in particular the size of the head 8 is based on a three-dimensional surface image of the face obtained by three-dimensional scanners or cameras. Fitting a parametric three-dimensional model of the face onto the acquired data allows deriving the size.

Other alternative image processing methods for deriving the face shape can be used as well. It might, for instance, be useful to take image in the infrared wavelength range for identifying the outlines of the face by the temperature difference between the skin and the hair.

Moreover, other measurements, which allow to derive an estimate of the bony tissue thickness for a particular patient 4, can be integrated in such a system, like a height and weight measurement to derive the body mass index or a local bone thickness measurement, derived for instance through the measurement of the wrist width. These measurements could be obtained automatically with an additional set of sensors integrated into the apparatus.

From these parameters the operation parameters for the imaging process by the radiographic apparatus can be derived, following some specific optimization criteria.

These operational parameters can also be used as a preset reference for an automatic exposure control (=AEC) system, where at the beginning of the exposure a closed loop control of the average detector signal and adjustment of the operational parameters is made, with a limited range of variation around the preset operational parameters used as a reference.

A third method for using the sensing capabilities of the apparatus is directed towards a method for utilizing a multiplicity of two-dimensional image views or three-dimensional images or curvilinear surfaces to identify the profile of the true dental arch of the patient 4.

From the measurement of the morphology of the head 8, taken with one or more two-dimensional cameras, or with a three-dimensional camera, the shape of the dental arch of the patient 4 can be computed. For these purposes, an adequate statistical model, for instance a morphable model as disclosed in BLANZ and VETTER, can be adopted to relate the face shape measured on the image with the shape of the dental arch.

It is therefore a particular advantage of the third method that it provides a quantitative evaluation of the true shape of the dental arch of the patient 4.

The apparatus and the methods also provide a correct positioning of the patient 4 avoiding the errors which occur at the operation of panoramic X-ray equipments, in particular the errors associated with methods to identify the actual protrusion of the incisors and correct the positioning of the patient 4 accordingly or associated with methods for positioning of the theoretic target dental arch profile, following a subjective evaluation of the operator supported by light indicators or the like. The apparatus and the method allow an automatic correction of the positioning errors caused by the inclination of the incisors and the deviation between the labial end of the incisors determining the position of the incisors in the bite unit and the root of the incisors which determines the position of the dental arch profile. Thus there is no need for the system to adjust the panoramic projection movements and hence the layer in focus according to the imparted correction of the operator.

According to a fourth method for using the sensor capabilities of the apparatus, two-dimensional image views, three-dimensional image or three-dimensional surfaces of the head 8 are used to identify a region of interest 36 (=ROI) on the images as shown in FIG. 6. As the images and the apparatus are calibrated, the position of the region of interest 36 with respect to the apparatus can be automatically derived. The apparatus will be instructed by the clinical operator to modulate the X-ray exposure inside the region of interest 36, for instance increasing or decreasing the dose inside the region of interest 36 with respect to the outside. Hence, a higher signal-to-noise ratio (=SNR) or a lower dose are achieved in the selected region of interest 36.

The region of interest 36 can be identified by the operator, by various standard means, like, for instance, selecting a rectangular window over the displayed image. Since the apparatus is equipped with a set of cameras, the images taken by the set of cameras are used to identify a window, the region of interest 36, corresponding to an area with special properties. The region of interest 36 can, for instance, correspond to the local volume required for radiography or tomography or can be an area which has to be spared from radiation or an area which requires a higher dose.

The region of interest 36 can also be identified on the rotated image or through the following procedure: A morphable face model is created as in BLANZ and VETTER, which is fitted to the actual face image. This model is then rotated automatically by software until it assumes the optimal orientation for setting the region of interest 36.

If a three-dimensional camera is adopted, the model can be automatically rotated until it assumes the optimal orientation to set the region of interest 36.

For assisting the operator in setting the region of interest 36, face features can be automatically superimposed on the video image. For instance, these features can be a schematic representation of the dentition.

In consequence, it is a particular advantage of the fourth method that it provides a simplified method to select the desired region of interest 36 and automatically associate optimized modulation of the X-ray exposure factors.

According to a fifth method, two-dimensional image views, three-dimensional volume images or three-dimensional curvilinear surface images of the head 8 are used to obtain a picture of the head 8 to automatically identify anatomical districts which require different exposures. Examples of such anatomical districts are the transition region between soft and bony tissue in lateral cephalography and the region of the cervical spine in panoramic radiography or local tomography. In the first case, this information is used to decrease the dose in the frontal part of the head 8, where soft tissue is present. Thus the radiation exposure in the soft tissue regions can be reduced or eliminated. In the second case, the position of the cervical spine vary the X-ray modulation profile such that a uniform exposure is achieved on the entire image. If necessary, the sensitivity of the detector 3 can also be adjusted to the dose. In general, this kind of information is used to optimize the modulation of the X-ray exposure profile, so that any unnecessary radiation exposure is avoided in particular for both soft and bony tissue and also for other anatomical structures that must be preserved from high dose irradiation.

It should be noted that in radiography and in particular in cephalography achieving a clear display of both the bony and the soft tissue is a challenging task. Setting the ideal exposure parameters for both tissues with respect to a particular patient 5 is difficult in most cases because of the large difference between the absorption coefficients of the two tissues. As a result, underexposure of bone or overexposure of soft-tissue often occurs, making the identification of all the structures difficult.

A particular advantage of the apparatus operated according to the fifth method is that it provides an automated identification of specific anatomical districts such as the spine in panoramic radiography or the transition from soft to bony tissue in cephalography, where a modulation of the operational parameter of the radiation exposure is automatically performed, without requiring intervention or subjective evaluations by the operator.

In one embodiment of the fifth method a two-dimensional or three-dimensional view of the head 8 is used to automatically identify the morphology of the patient 4 and to modulate the intensity of the radiation emitted by the X-ray tube accordingly.

In a preferred embodiment of the fifth method, a frontal camera is mounted in an apparatus for panoramic radiography. Such an apparatus can be an apparatus similar to the apparatus 11 shown in FIG. 2. In this case, the position and size of the cervical spine can be identified by analyzing the patient images. The position of the spine can be identified by image processing techniques arranged for identifying the spine pattern directly and/or in relation with other anatomical structures like eyes, nose, and chin. The spine position can be used to modulate the X-ray exposure profile to compensate for higher absorption by the spine.

Another embodiment of the fifth method relates to cephalography. In this embodiment, an apparatus as the apparatus 19 shown in FIG. 3 might be used. A lateral image of the patient 4 is taken by the lateral camera 20. In this image, an adaptive parametric curve can automatically be fitted to the lateral profile of the patient 4. This can be carried out, for instance, by searching for a parametric curve which maximizes the norm of the gradient along the curve itself. From this curve a set of reference points, like for instance the nasion, can be automatically derived and used to automatically optimize the X-ray exposure, modulating the X-ray intensity during the acquisition such that both the soft and bony tissue are correctly exposed.

Exposure profiles, in terms of KV or mA for the voltage and the current of the tube 2 can automatically be set according to different criteria such as maximization of the contrast, maximization of SNR or minimization of the dose applied to the patient 4.

The sixth method is directed to a method in which the processing of the acquired radiographic image produces as an output a synthesized lateral view of the skull of the patient 4 with an overlay of the radiographic images and camera views supporting the identification of the morphological landmarks of the patient 4 with particular regard to soft tissues of the head 8. In particular two-dimensional image views or two-dimensional projections of three-dimensional surface images are superimposed over a two-dimensional radiographic image, to obtain a single image containing both the radiographic view and the video image with the visible anatomy in particular at the surface of the patient 4. The synthesized image is preferably obtained by utilizing the processing techniques used for image registration in artificial vision.

The synthesized image can help the operator to identify the patient morphological landmarks with particular regard to the soft tissues of the head 8, for instance nose, lips, chin. In this case, an accurate registration algorithm is needed to perform a reliable matching between the radiographic and image data.

The sixth method is preferably based on a lateral or frontal image of the head 8, or a combination thereof. The method uses the video image and the X-ray image, registered in space through an adequate and accurate calibration procedure. The method provides a single output image blending the two images as in WHITAKER. To increase the diagnostic significance of the images, the blending coefficient could be set to obtain the maximum visibility of the anatomical structures through an adequate algorithm.

The blending coefficients can be set automatically to a different value in different regions, according to local contrast evaluation, obtaining therefore a blending field. Blending coefficients can be obtained for instance by maximizing the visibility of both soft and bony tissues in X-ray images as in WHITAKER or in FROSIO, FERRIGNO and BORGHESE.

Three-dimensional images can be used alternatively to two-dimensional images. In this case the three-dimensional image can be projected over the X-ray image at an arbitrary orientation.

Another embodiment of the present invention is directed to analyze the effect which has the modification of the bone structure, following maxillo-facial or plastic surgery, on the soft tissue and, in turn, on the face aspect. In fact, after registration of the visible image onto the radiograph image, the mixed image can be locally stretched coherently with the anatomical modifications introduced by the surgery to highlight the effect of the surgery onto the anatomy of the patient 4.

A particular advantage of the sixth method is the possibility to process and combine the information of the radiographic views and the camera views in order to obtain a synthesized image that can be used by the operator to identify the morphological landmarks of the patient 4 with particular regard to the soft tissues of the head 8, in particular nose, lips and chin.

The various apparatus described herein and the various methods of operating these apparatus provide a number of advantages:

If the apparatus are equipped with biometric sensor, an identification of the patient 4 can be performed on-line, rapidly and safely. Accordingly the operator must not manually input the data of the patient 4 in a computer system as in equipments of the prior art that are often complemented with computer systems to register the patient data necessary for patient identification. Security procedures can be adopted to ensure adequate storage and retrieval of patient data to avoid mix up and confusion.

To obtain a maximum image quality, avoiding at the same time the irradiation of important anatomical tissue, the X-ray beam can be limited to small areas of the patient 4, which constitute the volume of interest. More generally, the intensity of the X-ray beam can be modulated to achieve the maximum signal-to-noise ratio in the area of interest, and the minimum dose released in the important tissues. This is for instance required in local tomography, but it can be desirable also when partial panoramic or cephalometric imaging is performed.

The apparatus and the methods allow the operator to choose the region of interest freely. In this respect the choice is not limited to a given set of trajectories, for example aimed at imaging a limited area of the mouth in orthopantomography or intended to take half panoramic radiographies or radiographies of a condyle. In all these cases, the clinical operator can only select a fixed region of interest 36, which is subsequently acquired. With the apparatus described herein the clinical operator can select any portion of the mouth as the region of interest 36. Moreover, he can chose whether the region of interest 36 should receive a higher dose to increase the signal-to-noise ratio in this area or a lower dose to preserve some important tissue, for instance the spine. This is typically achieved by subdividing the image into a predefined set of bands.

The present apparatus is not only equipped with a set of predefined discrete operational parameters, for instance a set of voltage and current pairs of the X-ray tube, appropriate for the different sizes, for instance "small", "medium", "large", to achieve a good exposure for patients 4 of different sizes. So there is no need that the clinical operator chooses one of the default configurations after a visual inspection of the patient 4. Furthermore, there is no need that the operator further manually modifies the exposure parameters on the basis of his personal evaluation of the size of the patient 4. Instead the operational parameters of the radiation exposure are determined automatically wherein the values of the operational parameters generally can be determined freely. Thus the operational parameter can assume any value within an allowable range and can be continuously or at least gradually adjusted to the required value using more than tree steps.

Also the mechanical parameters of the radiation exposure can be determined appropriately even if the anatomy of the patient 4 differs from predefined standards which are derived from experimental data. For example in orthopantomography the shape and the size of the focused surface should coincide with the dental arch of the patient 4. The methods and the apparatus described herein ensures that the focused surface coincides with the anatomical section of interest; as a consequence, blurred radiographic images with poor diagnostic meaning are avoided. Also the subjective evaluation of the patient dental arch is avoided. Such a subjective evaluation may otherwise lead to a selection of a panoramic projection with a modified path of the layer in focus, not necessarily adequate for the specific morphology of the patient 4.

With the apparatus and the methods described herein the resulting accommodation of the layer in focus to the specific morphology of the patient 4 generally leads to optimal results. The suggested method represents a considerable improvement in comparison to conventional methods in which the dental arch profile is determined by a subjective evaluation of the operator supported by input means such as a preconfigured directory of profiles, or a tablet to draw the actual patient dental arch profile.

Thus, the methods and apparatus described herein and equipped with multiple devices for retrieving morphological data allow to facilitate and automate the imaging process, providing:

- before exposure, the automated identification of the specific anatomical features of the patient 4 and the optimized presetting of the exposure technique factors and projection geometry, tailored on the actual anatomy of the patient 4;
- during exposure, the optimized X-ray dose modulation, either automatically or selected by the operator, in order to correctly expose the various regions of interest 36, and accordingly impart reduced dose to other body parts, according to the actual anatomy of the patient 4 and imaging requirements;
- after exposure, the possibility to complement the radiographic image with additional information about the internal and external anatomy, providing valuable tools for the medical analysis and diagnosis.

Finally it should be noted that throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

What is claimed is:

1. An apparatus for taking radiographic images of a patient comprising:
    - an imaging system having a high energy radiation source and a high energy radiation detector;
    - a patient support system to position a patient in a predefined position with respect to the imaging system,
    - at least one data acquisition device arranged to be used in connection with the generation of biometric data on the actual anatomy of the patient; and
    - a control unit adapted for controlling an imaging process in dependency of the biometric data, characterized in that the at least one data acquisition device is arranged for the acquisition of multiple raw data regarding the anatomy of the patient and that
    - the control unit is arranged for identifying specific anatomical features of the actual anatomy of the patient by processing the multiple raw data, and for determining the multiple biometric data with respect to the identified specific anatomical features.

2. The apparatus according to claim 1, wherein a plurality of morphological parameters of the anatomy of the patient are obtainable as multiple biometric data.

3. The apparatus according to claim 1, wherein a profile of the anatomy of the patient is obtainable as multiple biometric data.

4. The apparatus according to claim 1, wherein the at least one data acquisition device is arranged for acquiring morphological raw data as multiple raw data in a contactless way.

5. The apparatus according to claim 4, wherein the at least one data acquisition device arranged for the acquisition of the morphological raw data is at least one device selected from the group comprising cameras adapted for taking views of the actual anatomy of the patient, devices adapted for taking three-dimensional images, devices which measure the traveling time of an acoustic or an electromagnetical signal in the radiofrequency or optical frequency range, or devices arranged for detecting a silhouette of the patient.

6. The apparatus according to claim 5, wherein the apparatus is provided with a mirror arrangement providing an additional perspective of the patient for the acquisition of the morphological raw data.

7. The apparatus according to claim 1, wherein the multiple raw data include anatomical raw data measured in contact with the patient.

8. The apparatus according to claim 7, wherein, for generating the anatomical raw data measured in contact with the patient, the apparatus is provided with devices selected from the group comprising devices adapted for measuring a movement or an acceleration of the patient.

9. The apparatus according to claim 1, wherein the apparatus is provided with a further data acquisition device acquiring biometric data and wherein the control unit is arranged for setting at least one operational parameter of the imaging process in dependency of the additional biometric data measured by the further data acquisition device.

10. The apparatus according to claim 9, wherein the further data acquisition device is arranged for measuring a weight or a length.

11. The apparatus according to claim 10, wherein the further data acquisition device is arranged for determining a body height of the patient by the height at which the positioning system is adjusted for the patient.

12. The apparatus according to claim 1, wherein the control unit is arranged for processing the multiple raw data using statistical pattern matching for identifying the anatomical features.

13. The apparatus according to claim 1, wherein the control unit is arranged for using the biometric data to automatically set at least one of the operational parameters selected from the group of operational parameters including current and voltage of the radiation source (2), exposure timing and projection geometry, scanning speed of the imaging system and sensitivity of the detector according to the actual anatomy of the patient.

14. The apparatus according to claim 1, wherein the control unit is arranged for setting at least one operational parameter of the imaging process using at least one optimization criterion.

15. The apparatus according to claim 14, wherein the control unit is arranged for using the minimization of the dose of the patient under the condition of a given signal-to-noise ratio of the signals of the detector as optimization criterion.

16. The apparatus according to claim 1, wherein the control unit is arranged for using at least one of the automatically set operational parameters as a preset reference for an automatic exposure control method, wherein at the beginning of the exposure time an adjustment of the operational parameter is made by a closed loop control of the operational parameter depending on the average signal of pixels of the detector while allowing a limited range of variation around a preset reference value of the operational parameter.

17. The apparatus according to claim 1, wherein the control unit is arranged for using the raw data and/or biometric data for providing an automatic identification of the patient.

18. The apparatus according to claim 1, wherein the control unit is arranged for using the raw data and/or biometric data for providing an automatic identification of the true dental arch of the patient.

19. The apparatus according to claim 1, wherein the control unit is arranged for using the raw data and/or biometric data for an automatic determination of the spine position of the patient and for using the identified spine position to homogenize or adjust the level of exposure of the detector by automatically modulating the radiation intensity profile during the imaging process.

20. The apparatus according to claim 1, wherein the control unit is arranged for using the raw data and/or biometric data are for providing an automatic identification of the patient face transition from soft to bony tissue for use in lateral radiographic images of the head of the patient and wherein the control unit is arranged for using the identified transition from soft to bony tissue to homogenize the level of exposure or to avoid the radiation exposure of the soft tissue region by automatically modulating the radiation intensity profile or adjusting the detector sensitivity during the acquisition of the radiographic images of the skull of the patient.

21. The apparatus according to claim 1, wherein the control unit is arranged for using the raw data and/or biometric data for providing as an output the actual protrusion of incisors and wherein the control unit is arranged for automatically correcting the positioning errors caused by the inclination of the incisors and the deviation between the labial end of the incisors determining the position of the incisors in the positioning system and the root of the incisors, which determines the position of the dental arch profile.

22. The apparatus according to claim 1, wherein the control unit is arranged for using the raw data and/or biometric data for providing a two-dimensional or three-dimensional display of the anatomy of the patient and wherein the control unit is arranged for limiting the imaging process to a region of interest selected by the operator using a display of the patient anatomy.

23. The apparatus according to claim 22, wherein the control unit is arranged for using the selected region of interest to automatically control the imaging process, in order to perform either a partial acquisition limited to the region of interest or an acquisition with a differentiated operational parameter inside or outside of the region of interest, according to the preference of the operator.

24. The apparatus according to claim 1, wherein the control unit is arranged for processing the radiographic images and for using the raw data and/or biometric data for improving the image quality of the radiographic images.

25. The apparatus according to claim 1, wherein the control unit is arranged for using the biometric data for providing additional information supporting the medical diagnosis.

26. The apparatus according to claim 1, wherein the control unit is arranged for processing the acquired radiographic image and for producing as an output a synthesized lateral view of the skull of the patient with superimposed radiographic views and details of a camera view supporting the identification of morphological landmarks of the patient.

27. The apparatus according to claim 1, wherein the control unit is arranged for obtaining the synthesized image by using an image registration process.

28. The apparatus according to claim 1, wherein the radiographic imaging system is arranged for dental panoramic radiography, dental tomography, cephalography or mammography.

* * * * *